(12) United States Patent
Howard

(10) Patent No.: US 10,016,066 B2
(45) Date of Patent: Jul. 10, 2018

(54) INFANT STABILIZING AND IMMOBILIZATION APPARATUS

(71) Applicant: No More Squirmy Baby, LLC, Tampa, FL (US)

(72) Inventor: William Howard, Tampa, FL (US)

(73) Assignee: NO MORE SQUIRMY BABY, LLC, Tampa, FL (US)

(*) Notice: Subject to any disclaimer, the term of this patent is extended or adjusted under 35 U.S.C. 154(b) by 473 days.

(21) Appl. No.: 14/713,303

(22) Filed: May 15, 2015

(65) Prior Publication Data
US 2015/0327689 A1 Nov. 19, 2015

Related U.S. Application Data

(60) Provisional application No. 61/993,539, filed on May 15, 2014.

(51) Int. Cl.
| | | |
|---|---|---|
| A47D 5/00 | (2006.01) |
| A47D 15/00 | (2006.01) |
| A61F 5/37 | (2006.01) |
| A61G 1/044 | (2006.01) |

(52) U.S. Cl.
CPC .............. *A47D 5/00* (2013.01); *A47D 15/00* (2013.01); *A47D 15/005* (2013.01); *A61F 5/3723* (2013.01); *A61G 1/044* (2013.01)

(58) Field of Classification Search
CPC .......... A47D 5/00; A47D 5/003; A47D 5/006; A47D 15/00; A47D 15/005; A61F 5/3723; A61F 5/3769; A61F 5/3776; A61G 7/0504; A61G 1/044
See application file for complete search history.

(56) References Cited

U.S. PATENT DOCUMENTS

| | | | | | |
|---|---|---|---|---|---|
| 1,502,276 | A | * | 7/1924 | Siebert | A47D 15/008 128/875 |
| 2,102,281 | A | * | 12/1937 | Pringle | A47D 15/008 128/875 |
| 2,245,293 | A | * | 6/1941 | Ogburn | A61F 5/3761 128/878 |
| 2,547,466 | A | | 4/1949 | Hoder | |
| 2,594,883 | A | * | 4/1952 | Donnen | A47D 15/008 128/870 |
| 2,848,993 | A | * | 8/1958 | Terrell | A61F 5/3784 128/875 |
| 3,215,834 | A | * | 11/1965 | Tayman | A61B 6/0421 119/754 |

(Continued)

OTHER PUBLICATIONS www.universalmedicalinc.com, Universal Metal Inc., "One Piece Wraparound Arm Board Velcro Restraint Strap", Product Code: 7419-19.

(Continued)

*Primary Examiner* — Robert G Santos
*Assistant Examiner* — David R Hare
(74) *Attorney, Agent, or Firm* — Shumaker, Loop & Kendrick, LLP; Jeffrey B. Fabian

(57) ABSTRACT

An immobilization apparatus that includes a base configured to support an infant laying the supine position; one or more straps affixed to the base; a locking mechanism for connecting the one or more straps across an infant's torso; and a fastener means for connecting strap segments to releasably secure an infant's extremities.

9 Claims, 14 Drawing Sheets

(56) References Cited

U.S. PATENT DOCUMENTS

| | | | | |
|---|---|---|---|---|
| 3,323,150 | A | 6/1967 | Rehder | |
| 3,324,851 | A * | 6/1967 | Posner | A61F 5/3723 128/878 |
| 3,474,781 | A * | 10/1969 | Gaylord, Jr. | A61F 5/3784 128/876 |
| 3,535,719 | A * | 10/1970 | Murcott | A61F 5/3776 128/876 |
| 3,650,523 | A * | 3/1972 | Darby, Jr. | A61F 5/3707 128/870 |
| 3,779,540 | A * | 12/1973 | Boudreau | A47D 15/008 128/876 |
| 3,856,004 | A * | 12/1974 | Cox | A61F 5/05808 128/DIG. 19 |
| 4,172,453 | A * | 10/1979 | Leckie | A61F 5/3723 128/876 |
| 4,205,669 | A * | 6/1980 | Hamann | A47D 5/00 5/424 |
| 4,414,969 | A * | 11/1983 | Heyman | A61F 5/3761 128/878 |
| 4,481,942 | A | 11/1984 | Duncan | |
| 4,712,258 | A * | 12/1987 | Eves | A47D 5/006 5/420 |
| 4,858,625 | A * | 8/1989 | Cramer | A61F 5/3784 128/872 |
| 4,960,280 | A * | 10/1990 | Corder, Jr. | A63B 69/0059 273/DIG. 30 |
| 5,012,821 | A * | 5/1991 | Tarver | A61F 5/3761 128/876 |
| 5,016,650 | A * | 5/1991 | Marlar | A61F 5/3723 128/846 |
| 5,086,758 | A * | 2/1992 | Schiek, Sr. | A61F 5/028 128/876 |
| 5,329,934 | A * | 7/1994 | Bowman | A47D 13/08 128/870 |
| 5,439,008 | A | 8/1995 | Bowman | |
| 5,566,413 | A * | 10/1996 | Webb | A47D 15/008 5/118 |
| 6,125,487 | A * | 10/2000 | Ive | A47D 5/006 5/603 |
| 6,499,165 | B1 | 12/2002 | Morgillo | |
| 6,708,356 | B1 * | 3/2004 | LaValle | A47D 15/008 128/872 |
| 6,755,198 | B2 * | 6/2004 | Parker | A47D 5/00 128/870 |
| 6,834,405 | B1 * | 12/2004 | Hillstead | A47D 15/008 128/872 |
| 6,935,342 | B2 * | 8/2005 | Larson | A61F 5/3723 119/770 |
| 6,966,087 | B2 | 11/2005 | Robinette | |
| 6,978,479 | B2 | 12/2005 | Thach | |
| 7,065,814 | B2 * | 6/2006 | Rutkowski | A47D 5/006 128/876 |
| 7,178,877 | B2 * | 2/2007 | Watson | A47D 5/00 297/484 |
| 7,337,482 | B2 * | 3/2008 | Byrne | A47D 15/008 128/872 |
| 7,603,732 | B2 | 10/2009 | Robles et al. | |
| 7,757,320 | B2 * | 7/2010 | Lord | A47D 5/00 5/425 |
| 8,117,698 | B1 | 2/2012 | Harry | |
| 8,127,385 | B1 | 3/2012 | Goutevenier | |
| 8,302,230 | B1 | 11/2012 | Jarrett, Jr. et al. | |
| 8,505,542 | B2 * | 8/2013 | Boxall | A61F 5/3761 128/879 |
| 8,602,032 | B2 * | 12/2013 | Goldsmith | A61F 5/3776 128/876 |
| 8,782,836 | B2 * | 7/2014 | Fort | A47D 15/008 128/870 |
| 8,910,332 | B2 * | 12/2014 | Buckson | A41B 13/06 5/482 |
| D743,186 | S * | 11/2015 | Perdue | D6/596 |
| 2006/0016013 | A1 * | 1/2006 | Lord | A47D 5/00 5/655 |
| 2006/0150330 | A1 | 7/2006 | Gatten | |
| 2006/0293623 | A1 | 12/2006 | Carroll | |
| 2010/0275377 | A1 * | 11/2010 | West | A61F 5/3776 5/621 |
| 2011/0209716 | A1 * | 9/2011 | Scarsbrook | A47D 5/00 128/872 |
| 2012/0216349 | A1 | 8/2012 | Kaplan et al. | |
| 2013/0206148 | A1 | 8/2013 | Hiebert | |
| 2016/0174731 | A1 * | 6/2016 | Pulley | A47D 15/005 128/878 |

OTHER PUBLICATIONS

"Grady Straps", http://en.wikipedia.or/wiki/Grady_straps (3 pages).

* cited by examiner

US 10,016,066 B2

INFANT STABILIZING AND IMMOBILIZATION APPARATUS

CROSS REFERENCE TO RELATED APPLICATION

This application claims priority from U.S. Provisional Application Ser. No. 61/993,539 filed May 15, 2014. The entirety of this provisional patent application is incorporated herein by reference.

TECHNICAL FIELD AND BACKGROUND

The present invention relates generally to stabilization devices, and more particularly, to an apparatus for stabilizing and immobilizing an infant during diaper changing.

Changing a diaper can be a difficult task. As babies learn to move about, they are less likely to remain still while lying on their backs. During changing, for example, babies often squirm about in an attempt to rollover, or they attempt to move in a head-wise direction using their feet to push off the changing surface. A caregiver is then required to use at least one hand to keep the baby stable while using the other hand to change the diaper. The caregiver must maintain constant attention on the baby to change the diaper and to ensure the baby's safety. This can be particularly challenging for single caregivers changing a diaper without assistance or for caregivers such as an infirm grandparent who might not possess the strength and dexterity needed to keep the baby stable with one hand while changing a diaper with the other. In addition to imposing a burden on the caregiver, the baby's movement creates significant hazards, such as the possibility that the baby could fall from an elevated changing surface.

Accordingly, it is an object of the present invention to provide a means for stabilizing and immobilizing the infant in the supine position during diaper changing. The stabilization and immobilization apparatus disclosed herein utilizes a one or more restraints to prevent an infant from squirming about or reaching for objects during diaper changing while also mitigating the possibility that an infant will crawl away or roll onto its stomach. The apparatus thus greatly assists caregivers with changing diapers and providing for the general care of an infant. Repeated use of the immobilization apparatus also has the added benefit of establishing a routine for an infant during diaper changing where the infant remains stable and immobile, thereby teaching the infant over time to remain still during changing.

SUMMARY

According to one embodiment of the invention, an immobilization apparatus includes a base; a locking mechanism; a first and second strap having a fixed segment attached to the base and the locking mechanism and a free segment attached to the locking mechanism; and at least one fastener means to releasably secure at least a portion of the fixed segments to at least a portion of the free segments.

In one aspect of the invention, the fastener means for the for the first and second straps comprises a first hook-and-loop-fastening surface disposed along at least a portion of the fixed segment length and a corresponding second hook-and-loop-fastening surface disposed along at least a portion of the free segment length so that the two segments can be releasably secured together. In another aspect of the invention, the immobilization apparatus includes a guard overlying a surface of the fastener means. In other embodiments, the fastener means is made of at least one snap fastener disposed along at least a portion of the first and second strap lengths.

According to a further aspect of the invention, the locking mechanism is a side-release snap-fastener. The locking mechanism can include a buckle for moving the locking mechanism along the length of the first strap. The straps can be formed with a fabric layer, a foam layer, and a webbing layer.

In yet another aspect of the invention, the base includes an impression to accommodate an infant. At least a portion of the base can be covered by a fabric covering.

According to another embodiment of the invention, the immobilization apparatus includes a base; a strap receiving element affixed to the second side of the base; and a strap having a fixed segment attached to the base and the locking mechanism, a free segment attached to the locking mechanism, and at least one fastener means to releasably secure at least a portion of the fixed segment to at least a portion of the free segment.

Another embodiment includes a base with a first side and a second side; a locking mechanism; a first and second strap affixed to the base and engaged with the locking mechanism; and at least one extremity restraint attached to the first strap. In one embodiment, the extremity restraint comprises a first hook-and-loop-fastening surface disposed along at least a portion of the first strap length and a corresponding hook-and-loop-fastening surface to releaseably engage the first hook-and-loop-fastening surface. In another embodiment, the extremity restraint is formed as a cuff secured to the first strap.

BRIEF DESCRIPTION OF THE DRAWINGS

Features, aspects, and advantages of the present invention are better understood when the following detailed description of the invention is read with reference to the accompanying figures, in which.

DETAILED DESCRIPTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete and will fully convey the scope of the invention and enable one of ordinary skill in the art to make, use, and practice the invention.

Disclosed is an apparatus for stabilizing and immobilizing an infant while changing a diaper. An apparatus according to one embodiment of the invention generally includes a cushioned base configured to seat an infant in the supine position and one or more restraints configured to stabilize the infant and immobilize the infant's torso and extremities during changing. The restraints can include one or more torso restraints to prevent the infant from squirming about, crawling away, or rolling onto its stomach during changing. The apparatus can also include one or more extremity restraints that prevent the infant from kicking or reaching for objects during changing while also further restricting the infant's ability to squirm about, crawl away, or roll over.

Although the inventive stabilization and immobilization apparatus is generally described with reference to restraining an infant during diaper changing, those skilled in the art will recognize that the apparatus can be used in a variety of circumstances where it is desired to stabilize or immobilize an infant, such as during the administration of medicine, feeding, changing clothes, or even after a medical procedure where movement could compromise sutures or have other negative effects. Additionally, while the present invention finds particular application in the field of restraining infants, a person of any age may be restrained by the stabilization and immobilization apparatus described in the embodiments below.

As used herein, the term infant is intended to generally describe a person under the age of three and is used interchangeably with the terms baby or child. The term caregiver denotes a person responsible for changing an infant's diaper or generally providing for the care and well-being of the infant, such as a parent, grandparent, babysitter, or healthcare professional. The term caregiver is used interchangeably with the terms parent, adult, user, or consumer. Wherever used herein, the masculine shall be deemed to include the feminine and the feminine shall be deemed to include the masculine.

Figure 1:
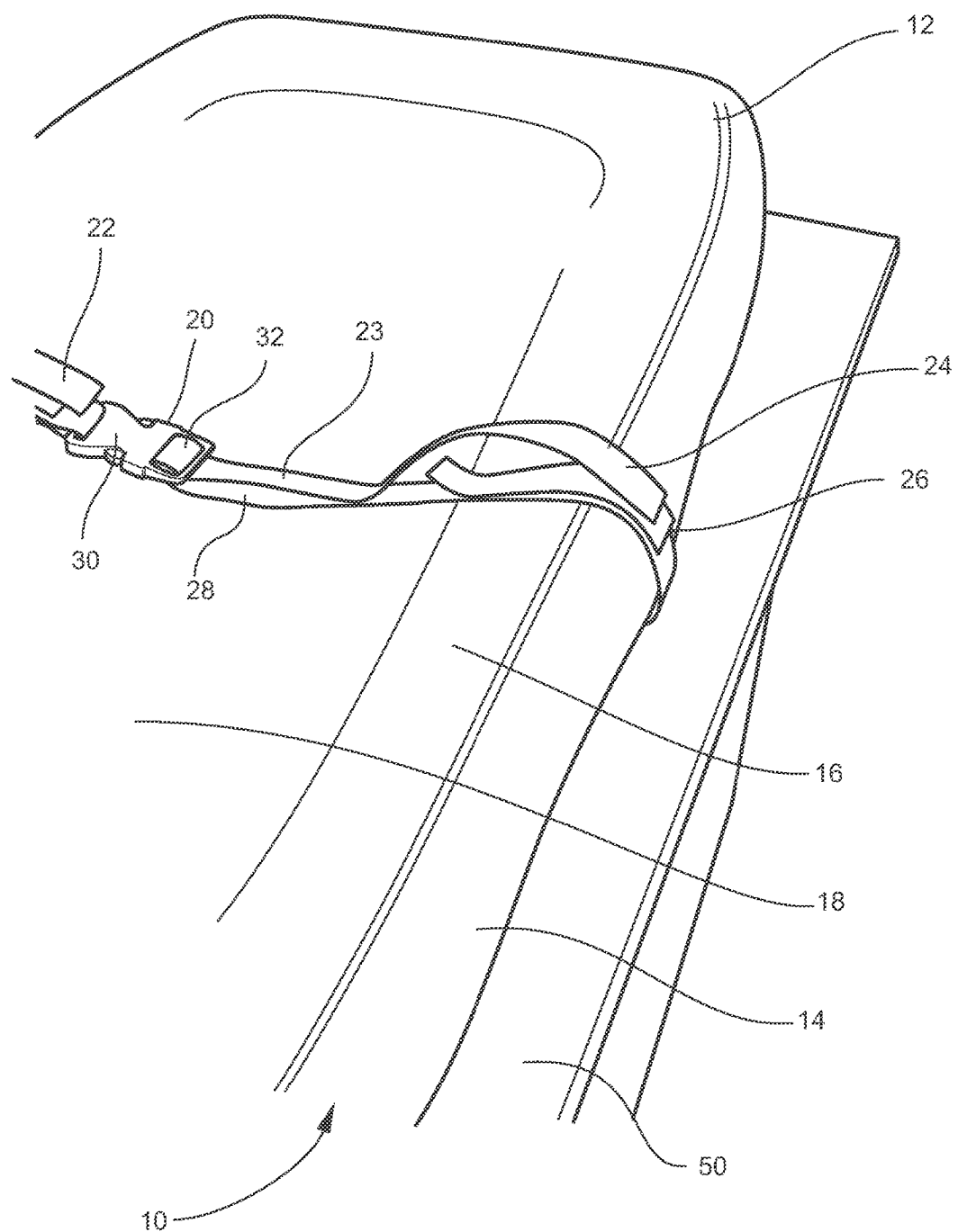
FIG. 1 is a stabilization and immobilization apparatus according to one embodiment.

Referring to FIG. 1, an exemplary stabilization and immobilization apparatus 10 according to one embodiment includes a cushioned base 12, a fabric cover 14, a torso restraint 20, and one or more extremity restraints 24. The base 12 is generally rectangular, has a length greater than its width, and is of predetermined dimensions suitable for accommodating an infant being immobilized. Preferably, the length of the base 12 is approximately the same, or greater than, the height of the infant, and the width of the base 12 is approximately the same, or greater than, the width of the infant's torso while her arms are resting by her side. In one embodiment, the width of the base 12 is approximately sixteen inches, and the length of the base 12 is between about thirty inches and thirty-four inches.

The base 12 should be thick enough to provide cushioning but thin enough such that the infant would not be injured if he or she rolled off the base 12 onto the changing surface 50 on which the stabilization and immobilization apparatus 10 is placed. The dimensions of the base 12 (e.g., length, width, and thickness) can be sized to ensure stability and to prevent the infant from tipping the entire stabilization and immobilization apparatus 10.

Figure 7:
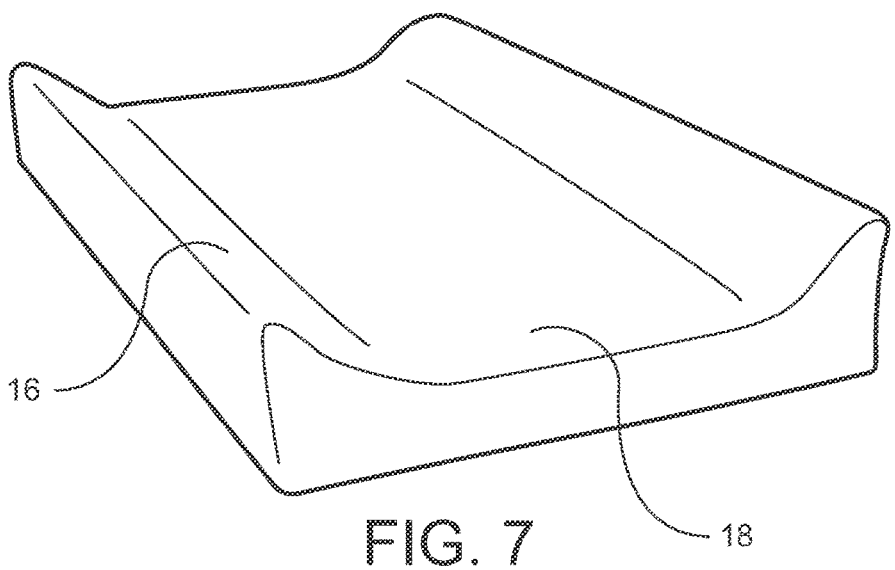
FIG. 7 illustrate an exemplary base with an impression for accommodating an infant.

As shown in FIGS. 1 & 7, the top surface of the base 12 can include an impression 18 suitable to accommodate the shape of an infant lying in the supine position. The impression 18 can be, for instance, generally rectangular or elliptical, or it can include separately shaped portions to accommodate the infant's head, torso, or extremities. The raised base sidewalls 16 surrounding the impression 18 further ensure the infant's safety and immobility by impeding the infant's ability to rollover off the base 12. The base sidewalls 16 can be sloped to provide for the comfort of the infant and to promote easier access to the infant by the caregiver.

Figure 8:
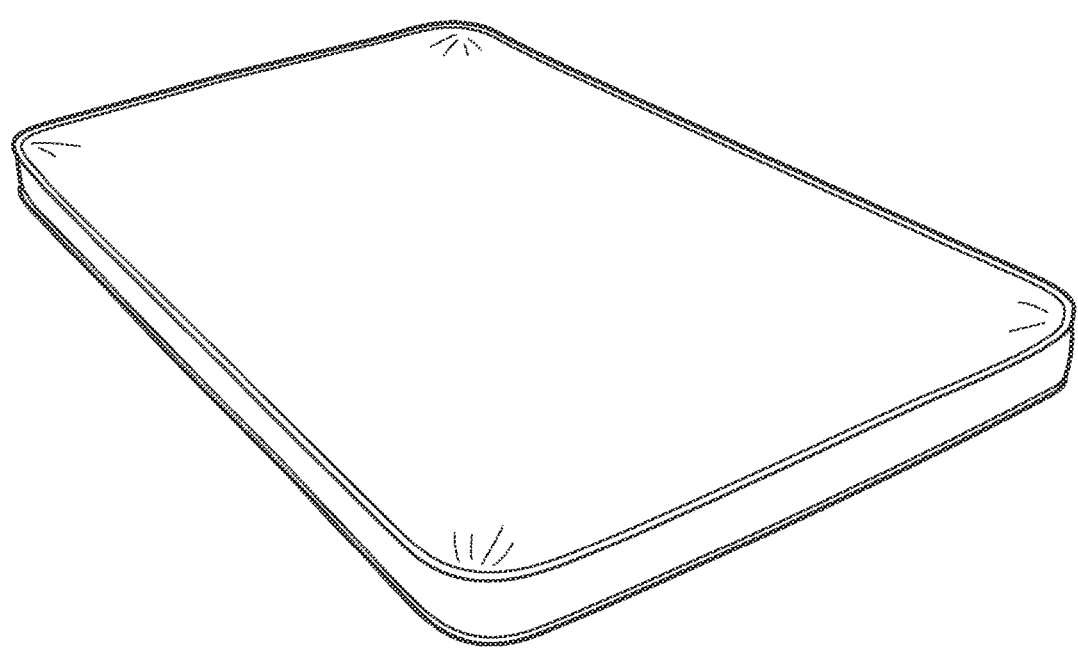
FIG. 8 illustrate an exemplary base with a flat surface.
Figure 9:
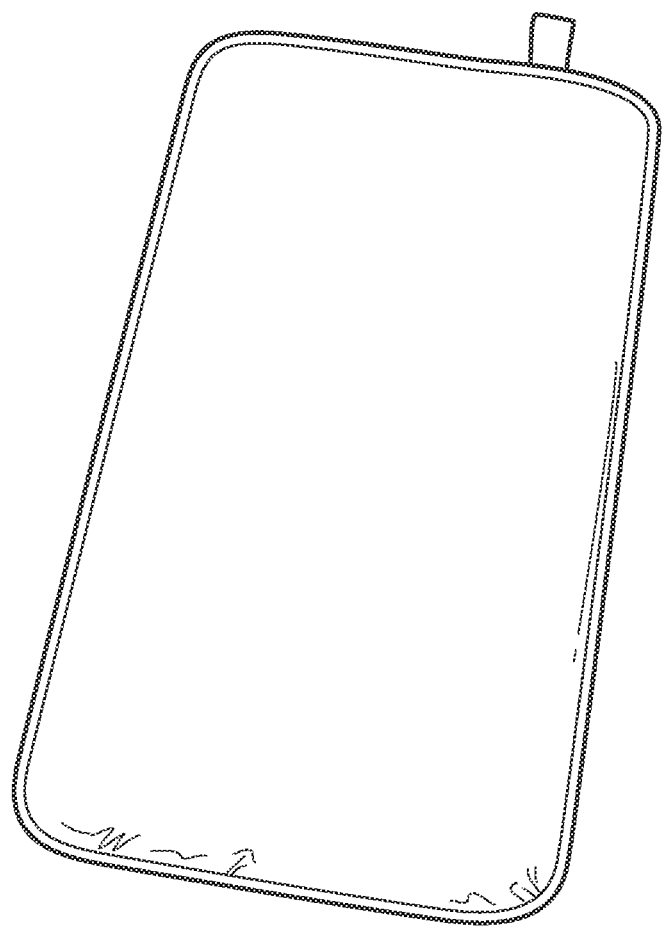
FIG. 9 illustrate an exemplary portable base with a flat surface.
Figure 10:
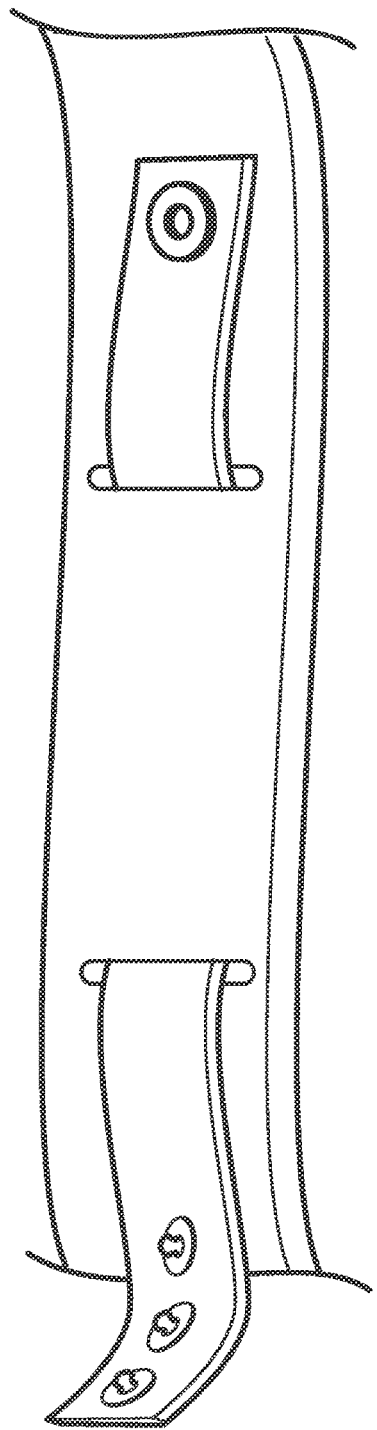
FIG. 10 illustrates an exemplary extremity restraint.
Figure 11:
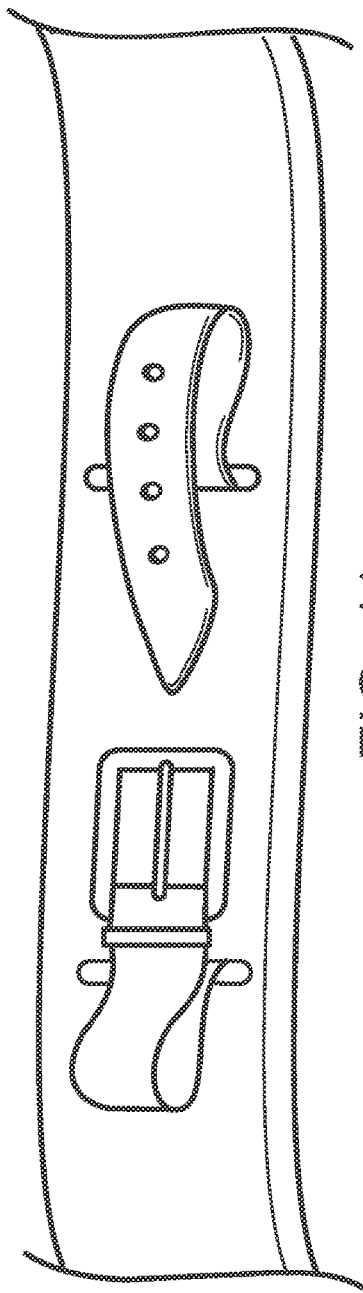
FIG. 11 is an exemplary extremity restraint.

Alternatively, the base 12 can be formed as a substantially flat pad if the impression 18 and sidewall 16 features are not desired, as illustrated in FIGS. 8-9. In other embodiments, the thickness of the base 12 can be reduced as shown in FIG. 9 so that the base 12 can be rolled or folded so as to reduce its dimensions for convenient transport and carrying of the stabilization and immobilization apparatus 10.

The base 12 embodiment illustrated in the accompanying figures is constructed as a unitary, substantially solid member. The interior of the base 12 can be made of any material rigid enough to hold the infant in place but soft enough to provide cushioning for the infant's comfort, such as expanded polystyrene foam, extruded polystyrene foam, polyurethane foam, polyethylene foam, latex foam, cotton batting, wool batting, polyester batting, plush, or any other suitable material known to one of ordinary skill in the art.

The base 12 is optionally covered in whole or in part by one or more layers of a fixed or removable fabric covering 14. The fabric cover 14 can be made from woven textiles, such as wool, cotton, velvet, or silk. Or the fabric cover 14 can be made from nonwoven textiles, such as plush, wool or acrylic felt, or a polypropylene fabric. The fabric cover 14 can also be a waterproof material, such as a natural or synthetic fabric treated with rubber, polyvinyl chloride, polyurethane, silicone elastomer, fluoropolymers, or wax. In one embodiment, the base 12 is covered in whole or in part by a waterproof fabric layer underneath a second, outer fabric layer. Preferably, the fabric cover 14 is made of a soft, washable, nonallergenic textile to present a clean, comfortable surface for contacting the infant.

The fabric cover 14 can be secured around the base 12 using any suitable means known to those of ordinary skill in the art, including, but not limited to, stitching, elastic bands, zippers, glue (adhesive), or hook-and-loop type fastening material (e.g., VELCRO®). The fabric cover 14 can optionally be secured directly to the base 12 by, for example, stitching or gluing the cover 14 to the bottom surface of the base 12. In another embodiment, the fabric cover 14 is releasably secured around the base 12 by forming the cover 14 so that it conforms to the shape of the base 12 and by inserting the base 12 into the cover 14 through an opening that is wholly or partially closeable by a zipper, hook-and-loop-fastening material, or elastic bands around the edges of the opening.

Figure 16:
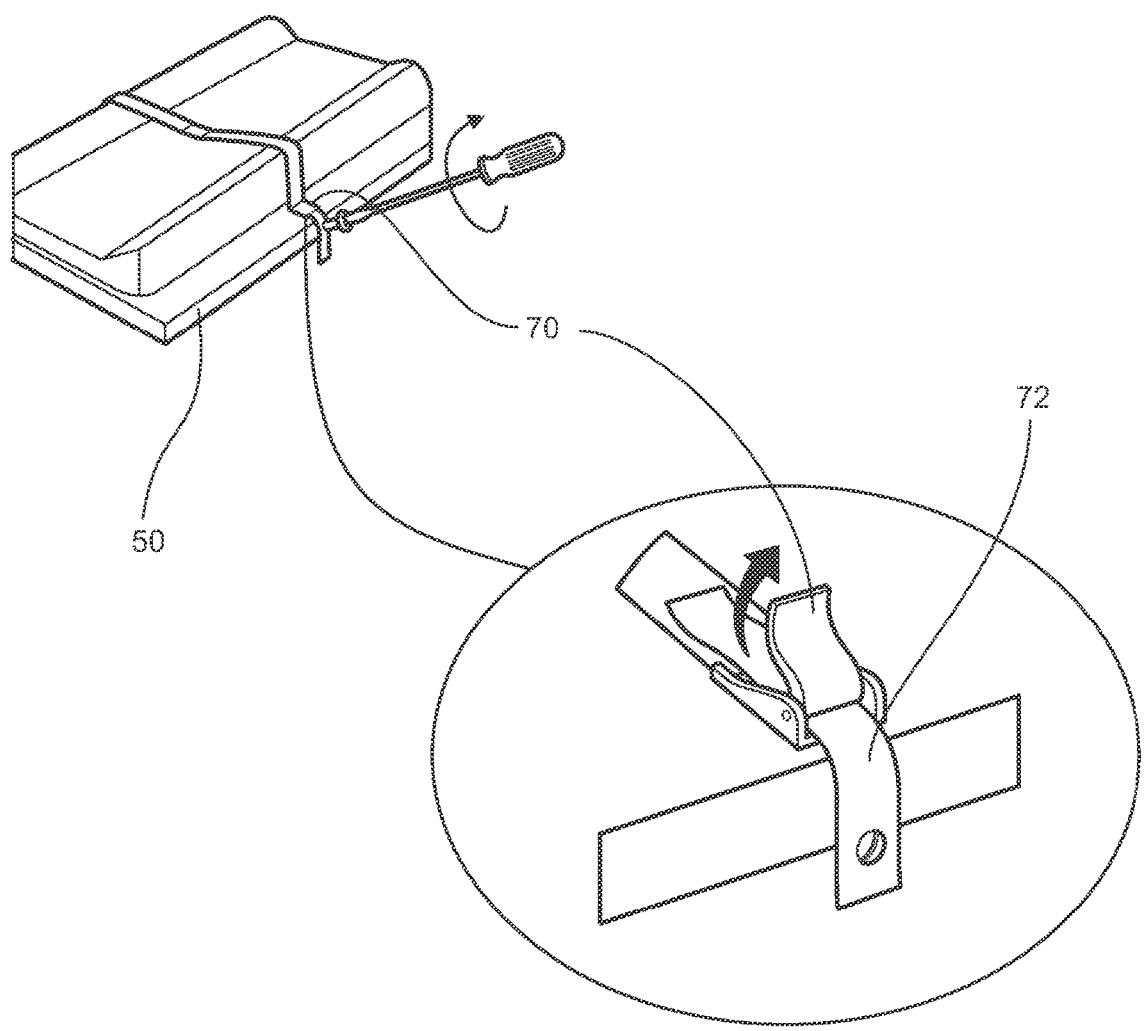
FIG. 16 is an exemplary anchor assembly.

Those of ordinary skill in the art will recognize that the base 12 embodiments depicted in the attached figures are not intended to be limiting, and other constructions and features are possible. By way of example, the base 12 can be formed as a pillow with filler material (e.g., polyester pellets, microbeads, feathers, etc.) enclosed by a fabric cover. In this embodiment, the base 12 may include a reinforcement member to provide added rigidity, such as a flexible plastic panel in the interior of the base 12. Yet another embodiment includes a plurality of slots or handles around the perimeter of the base 12 that serve as hand receptacles for convenient carrying of the stabilization and immobilization apparatus 10. The apparatus 10 can also include safety features, such as anchors 70 that secure the base 12 to the changing surface 50 via a fastening strap 72, as illustrated in FIG. 16. Further embodiments can include additional padding formed as contours on the base 12 to support various regions of the infant's body, such as a crescent-shaped pad to support the infant's head or a cylindrical pad to provide lumbar support.

The base 12 can also be comprised of multiple portions secured together by any suitable fastening means, such as when the base 12 includes separate portions to support the infant's head, torso, or extremities. In this manner, the stabilization and immobilization apparatus 10 can be adjusted to accommodate infants of different sizes or to accommodate a single infant as he or she grows. To illustrate, an additional base portion can be attached to the head of the base 12 shown in the attached figures using hook-and-loop-fastening material, straps, snap-fasteners, or the like, which effectively extends the length of the base 12 to accommodate infants of greater height. In one exemplary embodiment, the fabric cover 14 is an elastic material, such as spandex, nylon, or polyester, so that the fabric cover 14 can be stretched over an additional base portion.

The stabilization and immobilization apparatus 10 can include one or more straps that that run across the infant's chest, abdomen, or pelvic region to serve as torso restraints 20. The embodiments shown in FIGS. 1-3 include first strap 22 and a second strap 23 that connect over the infant's abdomen using a locking mechanism 30, such as corresponding male and female parts of a buckle, button, or snap-fastener.

Figure 2:
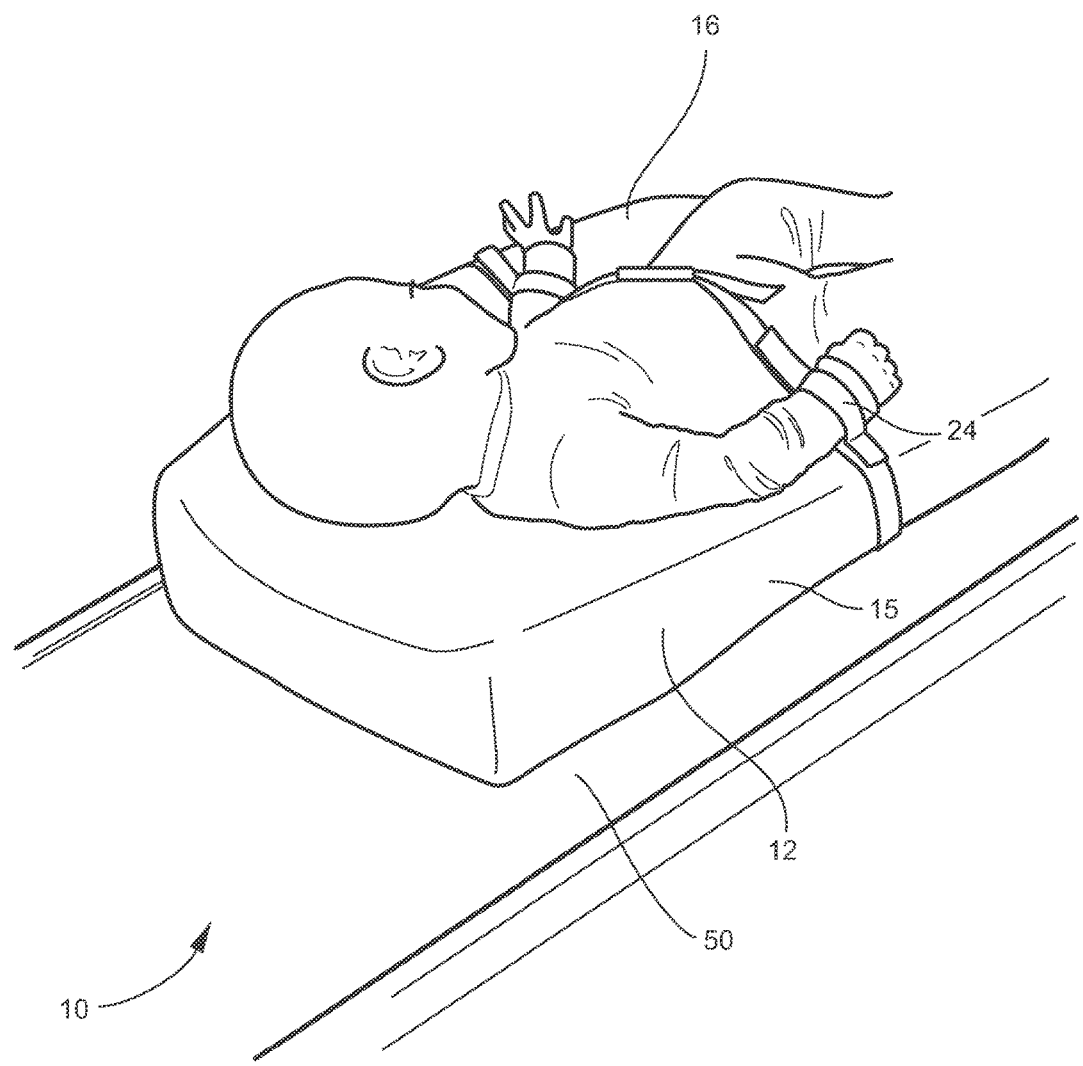
FIG. 2 shows an infant restrained in stabilization and immobilization apparatus according to one embodiment.
Figure 3:
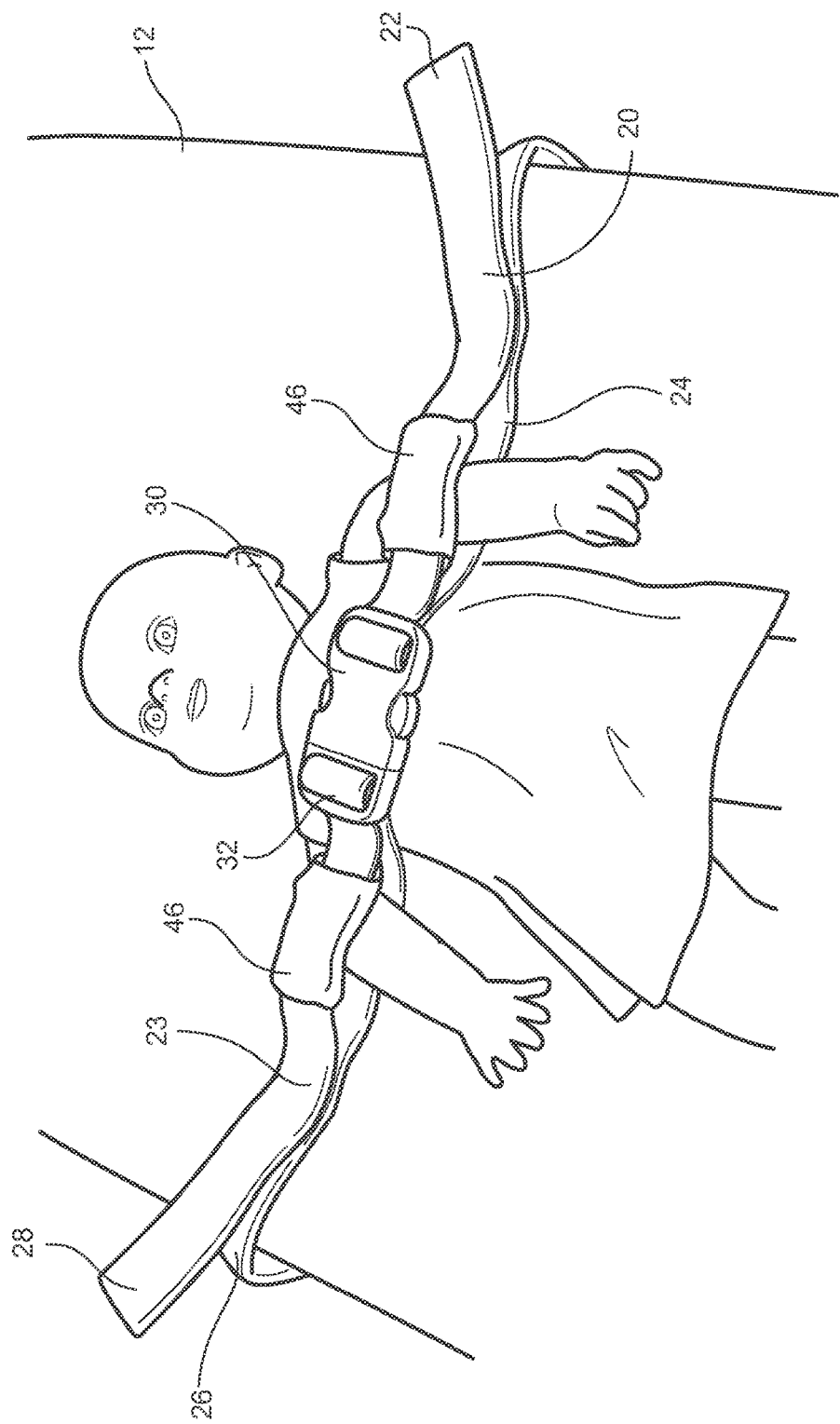
FIG. 3 is a stabilization and immobilization apparatus according to a second embodiment.
Figure 17:
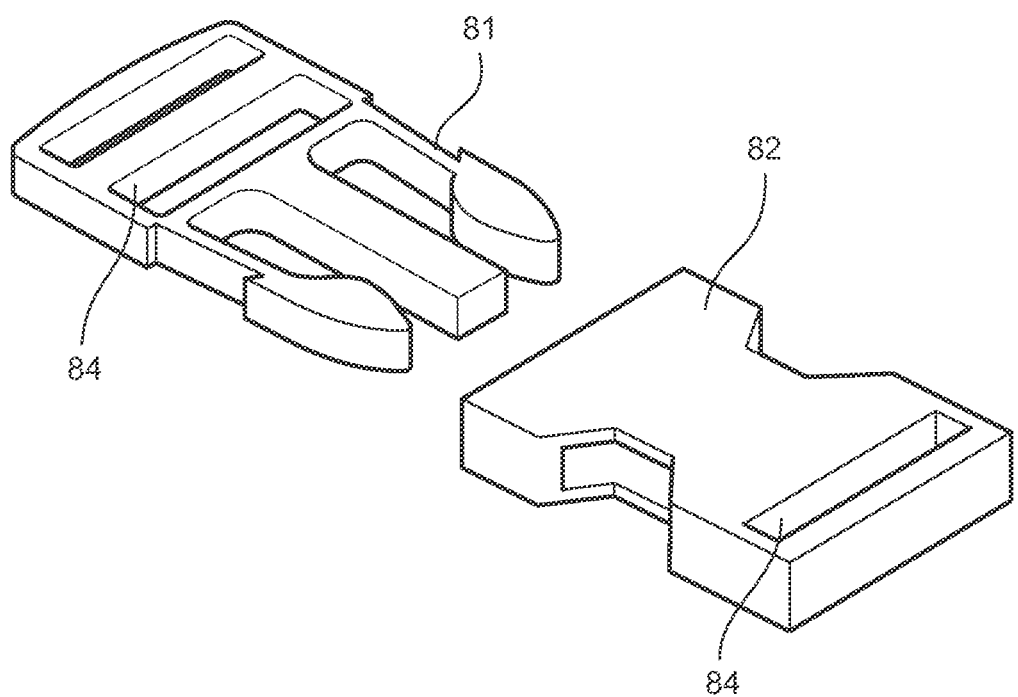
FIG. 17 is an exemplary side-release, snap fastener.

The first and second straps 22 & 23 include a fixed segment 26 affixed to the base sidewall 15 and engaged with the locking mechanism 30 and a free segment 28 engaged with the locking mechanism. The free segment 28 folds back over the fixed segment and releasably secures to the fixed segment 26 via a fastening means. The fixed segment 26 of each strap 22 & 23 is affixed to the base 12 and/or the fabric cover 14 by, for example, stitching, buttons, snap-fasteners, glue (adhesive), hook-and-loop-fastening material, or any other suitable affixing means. Exemplary straps 20 are shown in FIGS. 1-3 as straps that buckle across the infant's abdomen using a side-release, snap-fit buckle, such as the exemplary buckle shown in FIG. 17. The side-release buckle includes a male portion 81, a female portion 82, and an opening 84 for receiving a strap.

Figure 4:
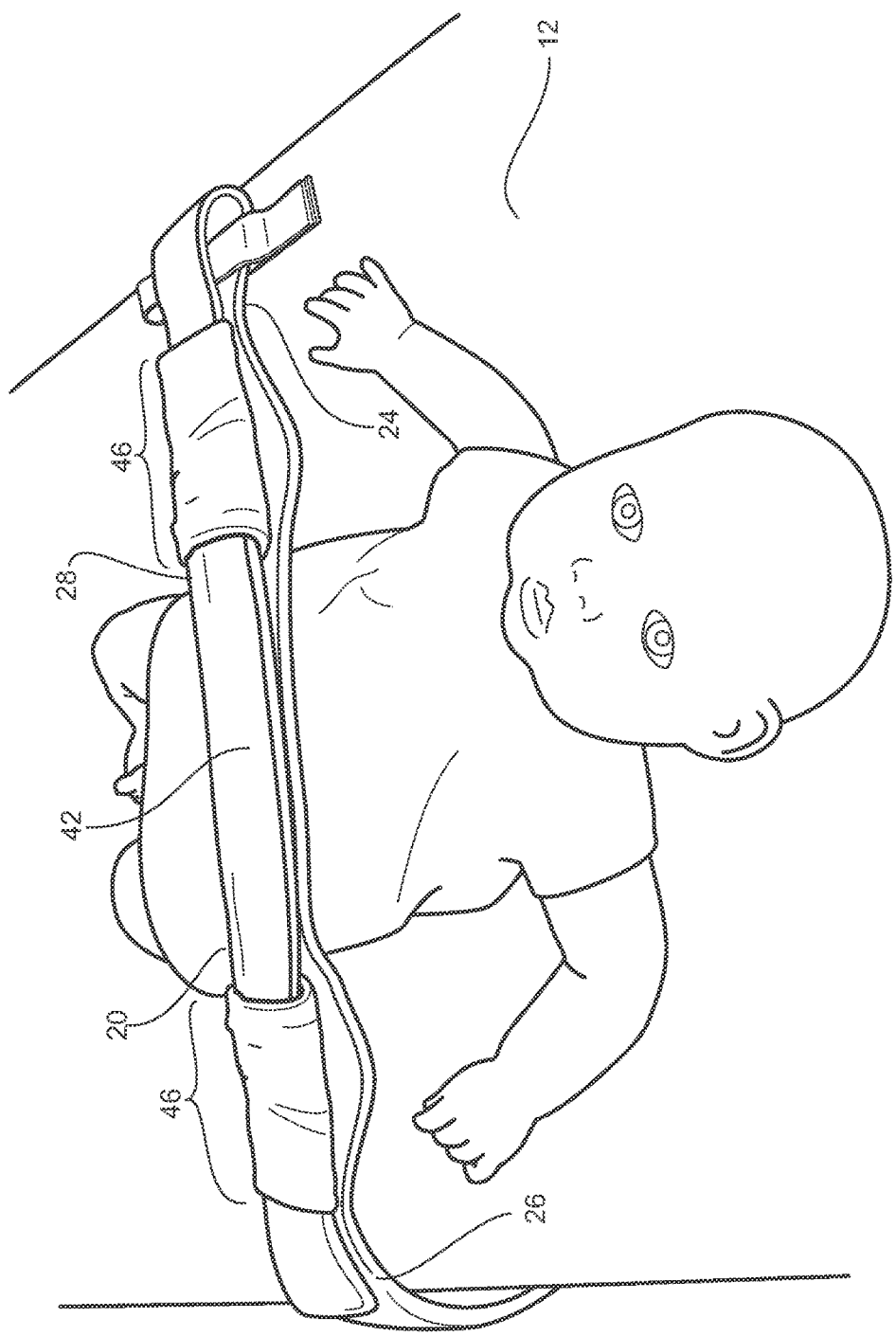
FIG. 4 is a stabilization and immobilization apparatus according to third embodiment.

The locking mechanism 30 includes a buckle 32 for adjusting the position of the locking mechanism 30 along the length of the straps 22 & 23, thereby effectively adjusting the length of the torso restraint 20 to secure infants of different sizes or to permit varying degrees of movement by the infant. The straps 22 & 23 can optionally be made of an elastic material to permit some degree of movement when the straps 22 & 23 are snug and secure across the infant. In other embodiments, the torso restraint 20 is formed as a continuous strap 42, as shown in FIG. 4. The continuous strap 42 includes a fixed segment 26 affixed to a base sidewall 15 and a free segment 28 that runs through a strap receiving element (e.g., a loop or buckle) on the opposite sidewall.

Figure 5:
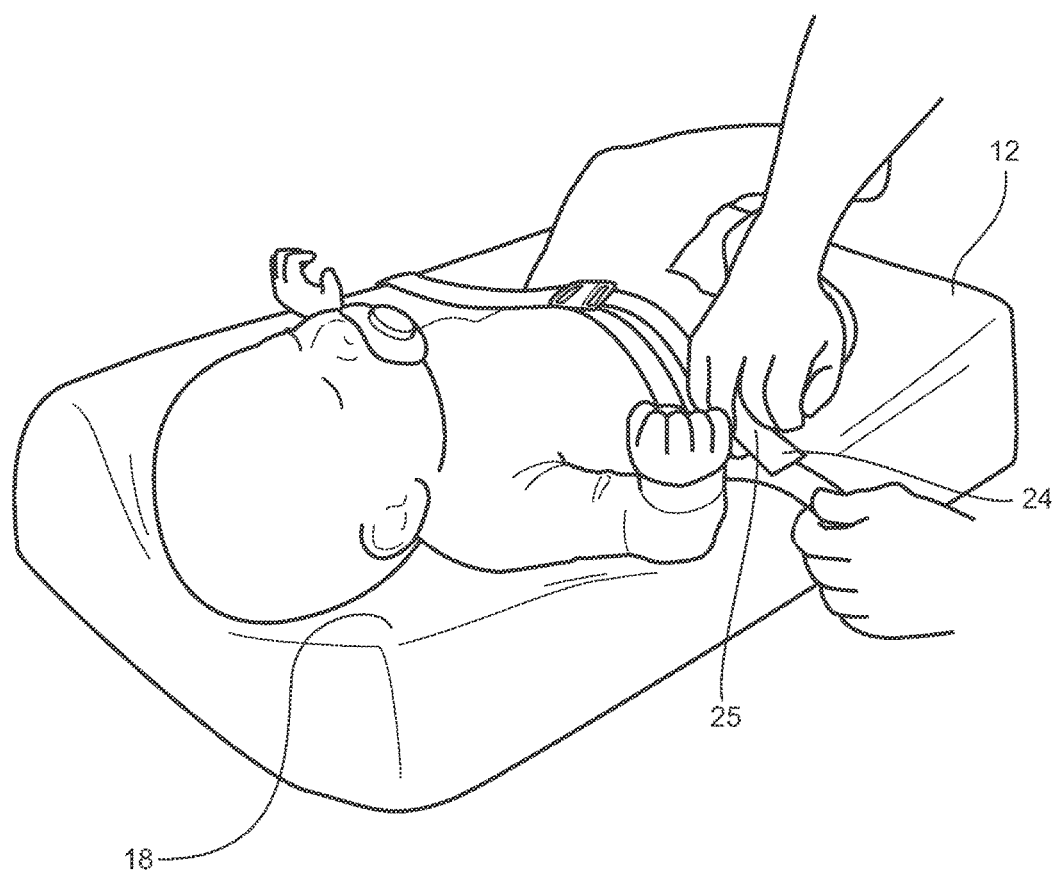
FIG. 5 illustrates the operation of a stabilization and immobilization apparatus.
Figure 6:
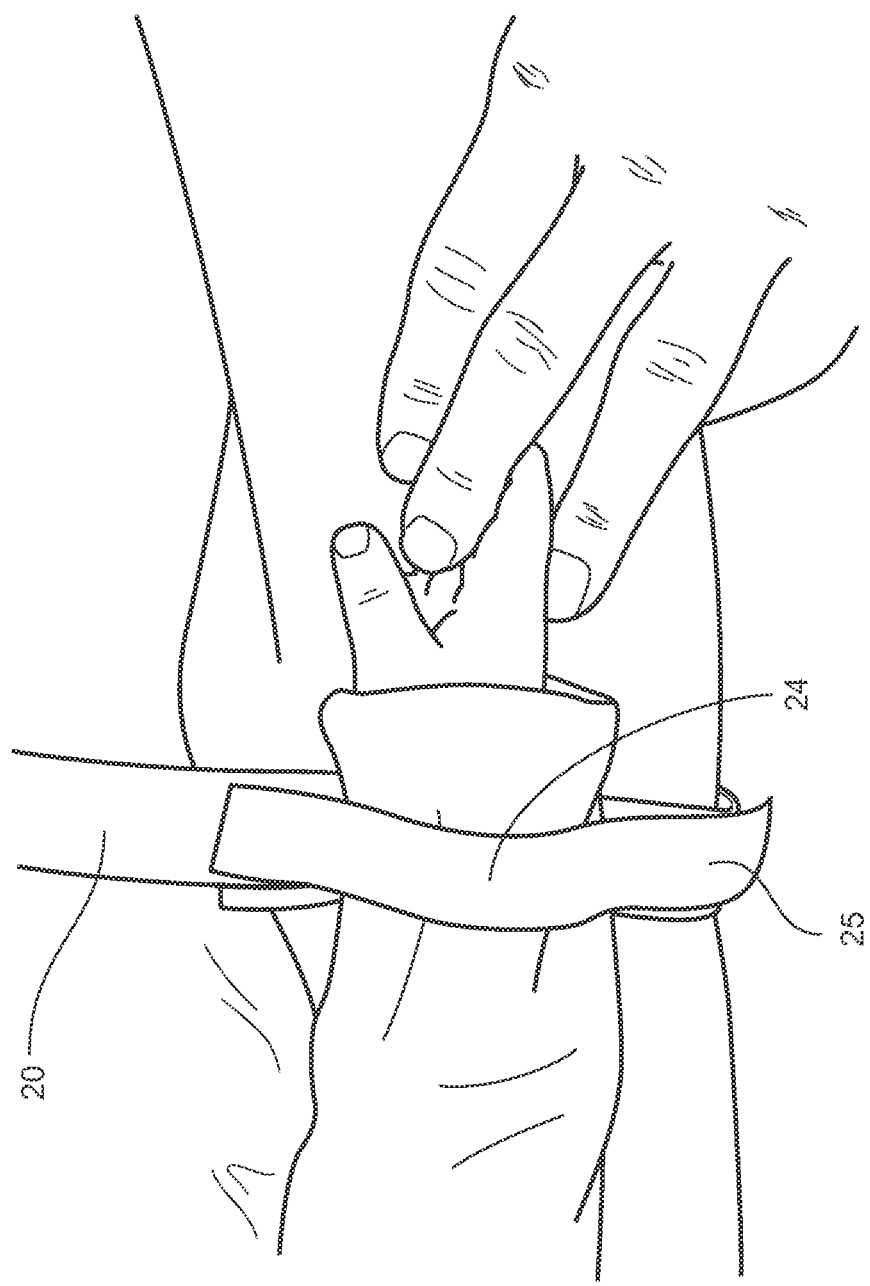
FIG. 6 illustrates an exemplary extremity restraint according to one embodiment of the invention.

The stabilization and immobilization apparatus 10 embodiment in FIGS. 1 and 5-6 includes one or more extremity restraints 24 formed from hook-and-loop-fastening material disposed along the length of the strap 22 & 23 free segments 28. The extremity restraints 24 restrict movement of the infant's arms, legs, hands, or feet and to prevent the infant from reaching for objects or kicking during diaper changing. The extremity restraints 24 are co-located with the torso restraint 20 and affixed to the torso restraint 20 using stitching, buttons, an adhesive, or any suitable affixing means.

As illustrated in FIG. 5, a first end 25 of the extremity restraint 24 is lifted upwards before placing the infant's arm between the two surfaces of the hook-and-loop-fastening material. The first end 25 of the extremity restraint 24 is reattached to the restraint to releasably secure the infant's extremity as shown in FIG. 6. The extremity restraints 24 may be placed around any suitable part of the infant's extremities, including the infant's wrists, forearms, upper arms, ankles, lower legs, or thighs. Placing the extremity restraint 24 around the infant's upper extremities, such as upper arm or thigh, has the advantage that it becomes more difficult for the infant to extract his or her extremities from the restraints 24.

The straps 22, 23, & 42 of the embodiments shown in FIGS. 3-4 include a fastener means to releasably secure the fixed segment 26 to the free segment 28, thereby forming an extremity restraint 24. The fastener means implemented as by disposing a hook-and-loop-fastening material along the length of the straps 22, 23, & 42 such that the strap segments 26 & 28 can be releasably secured together.

The hook-and-loop-fastening material may partially cover the straps 22, 23, & 42 so that the uncovered portion of the strap contacts the infant's extremities to provide for a comfortable fit. The hook-and-loop-fastening material should cover enough of the straps 22, 23, & 42 so that the length of the straps 22, 23, & 42 can be adjusted to accommodate infants of different sizes or to permit varying degrees of movement by the infant. The straps can include a guard 46, such as the fabric sleeve depicted in FIG. 4 to enhance comfort and safety. The guard can also be formed as a patch that covers a portion of the straps.

Figure 12:
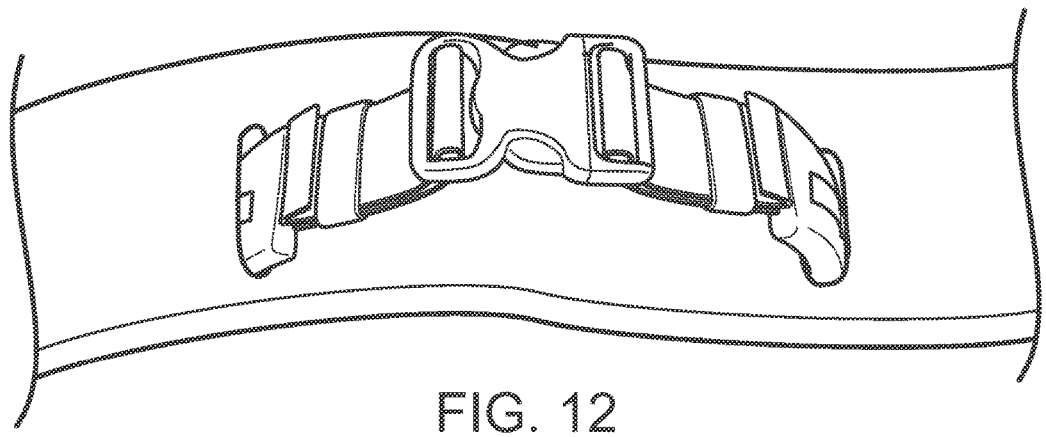
FIG. 12 is an exemplary extremity restraint.

Those of ordinary skill in the art will recognize that the embodiments described are not intended to be limiting, and other configurations for the torso 20 and extremity restraints 24 are possible. For instance, the exemplary extremity restraint 24 embodiments shown in FIGS. 10-13 are constructed as two separate straps connected together by snap buttons (FIG. 10), a peg and aperture buckle (FIG. 11), or a sliding snap-fit buckle (FIG. 12). By providing multiple buttons, apertures, or a sliding buckle along the length of the extremity restraint 24, the extremity restraint 24 can be adjusted to accommodate infants of different sizes or to permit varying degrees of movement. In other embodiments, the extremity restraint 24 can be constructed as a sliding hook and loop strap, such as the extremity restraint 24 depicted in FIG. 14.

Figure 13:
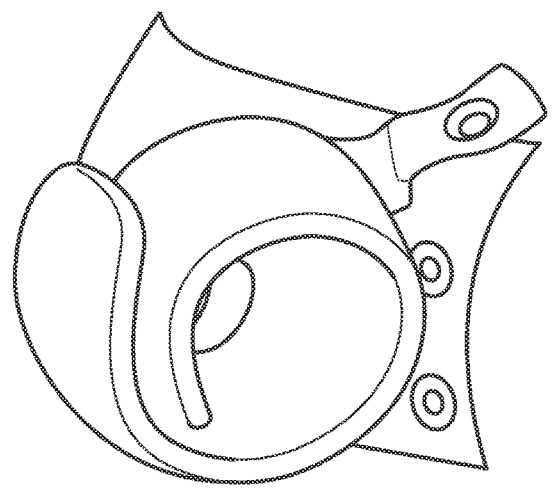
FIG. 13 is an exemplary extremity restraint.
Figure 14:
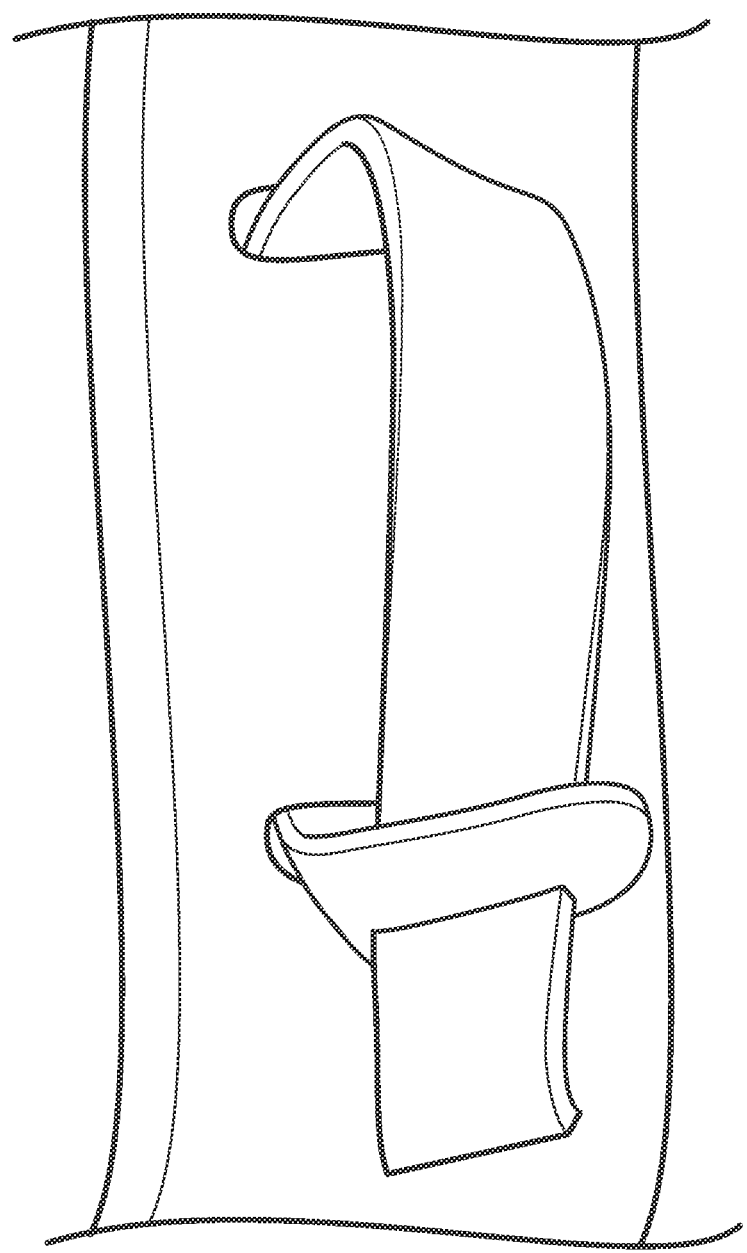
FIG. 14 is an exemplary extremity restraint.

The extremity restraints 24 can be integral with, or separable from, the torso restraint 20, such as when the extremity restraints 24 are separately affixed directly to the base 12 and/or fabric cover 14. The extremity restraints 24 can be attached to the torso restraint 20, base 12, and/or fabric cover 14 using any suitable fastening means, including, for example, a snap button, as illustrated in FIG. 13 or by stitching as shown in FIG. 14. By affixing one or more extremity restraints 24 to various locations on the torso restraint 20, base 12, and/or fabric cover 14, the extremity restraints can be configured to contact various locations on the infant's extremities, such as the infant's upper arm, forearm, wrist, thigh, lower leg, or ankle.

In one embodiment, the base 12 is configured so that extremity restraints 24 can be affixed to various locations along a sidewall 15 of the base 12. To illustrate, one or more components of a snap button fastener can be affixed to various locations on the base sidewall 15 so that the exemplary extremity restraint 24 shown in FIG. 13 can be snapped into a plurality of positions along the base sidewall 15.

Figure 15:
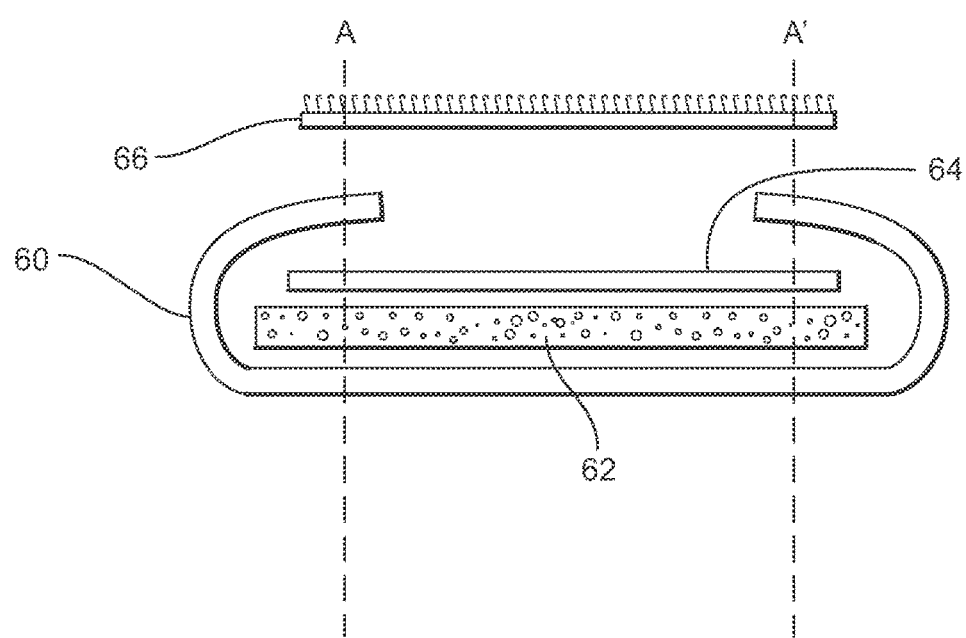
FIG. 15 illustrates the construction of a restraint strap according to one embodiment.

The restraint straps 22, 23, & 42 can be made from nylon, neoprene, polypropylene, cotton, vinyl, silk, leather, or any other suitable material known to one of ordinary skill in the art. The straps can be covered with a guard 46 as shown in FIG. 4 to provide for the infant's comfort and safety. The exemplary strap profile shown in FIG. 15 utilizes a multilayer design with layers of fabric 60, foam 62, webbing 64, and hook-and-loop material 66. The fabric 60 is folded over the foam 62 and webbing 64 and the layers are stitched along lines A and A' with the hook-and-loop material 66 serving as the outside layer.

Although the foregoing description provides embodiments of the invention by way of example, it is envisioned that other embodiments may perform similar functions and/or achieve similar results. Any and all such equivalent embodiments and examples are within the scope of the present invention.

What is claimed is:

1. An immobilization apparatus comprising:
   (a) a base with a first side and a second side;
   (b) a locking mechanism having a first part and a second part that releasably engages the first part;
   (c) a first strap comprising:
      (i) a first fixed segment affixed to the first side of the base and engaged with the locking mechanism first part, and
      (ii) a first extremity restraint comprising
         (A) a first free segment engaged with the locking mechanism first part, wherein the first free segment folds back over the first fixed segment; and
         (B) at least one fastener means to releasably secure a portion of the first fixed segment to a portion of the first free segment to form a first passage that is sized to accommodate a first extremity;
   (d) a second strap comprising:
      (i) a second fixed segment affixed to the second side of the base and secured to the locking mechanism second part, and
      (ii) a second extremity restraint comprising
         (A) a second free segment secured to the locking mechanism second part, wherein the second free segment folds back over the second fixed segment; and
         (B) at least one fastener means to releasably secure a portion of the second fixed segment to a portion of the second free segment to form a second passage that is sized to accommodate a second extremity.

2. The immobilization apparatus of claim 1, wherein the fastener means for the first and second straps comprises:
   (a) a first hook-and-loop-fastening surface disposed along at least a portion of a first fixed segment length and along at least a portion of a second fixed segment length; and
   (b) a second hook-and-loop-fastening surface disposed along at least a portion of a first free segment length and along at least a portion of a second free segment length, wherein if the first hook-and-loop-fastening surface is a loop surface, the second hook-and-loop-fastening surface is a hook surface, and if the if the first hook-and-loop-fastening surface is a hook surface, then the second hook-and-loop-fastening surface is a loop surface.

3. The immobilization apparatus of claim 2 further comprising a guard overlying the hook surface of the fastener means, wherein the guard is disposed between the hook surface and the loop surface when the portion of the fixed segment is secured to the portion of the free segment for the first strap and the second strap.

4. The immobilization apparatus of claim 2, wherein the locking mechanism is a side-release snap-fastener.

5. The immobilization apparatus of claim 4, wherein the locking mechanism first part further comprises a buckle for repositioning the locking mechanism first part along a length of the first strap.

6. The immobilization apparatus of claim 1, wherein the first and second straps comprise a foam layer secured between a fabric layer and a webbing layer.

7. The immobilization apparatus of claim 1, wherein the base further comprises an impression that accommodates an infant.

8. The immobilization apparatus of claim 1 further comprising a fabric cover covering at least a portion of the base.

9. The immobilization apparatus of claim 1, wherein the fastener means for the first and second straps comprises at least one snap fastener disposed along at least a portion of a first strap length and disposed along at least a portion of a second strap length.

* * * * *